United States Patent
Kreidl et al.

(10) Patent No.: US 7,094,904 B2
(45) Date of Patent: Aug. 22, 2006

(54) PROCESS FOR PREPARING MONOHYDRATE AND CRYSTAL MODIFICATIONS OF FLUCONAZOLE

(75) Inventors: Janos Kreidl, deceased, late of Budapest (HU); by Jánosné Kreidl née Regina Hegedus, legal representative, Budapest (HU); Laszlo Czibula, Budapest (HU); Csaba Szantay, Budapest (HU); Jenone Farkas, Budapest (HU); Ida Deutschne Juhasz, Budapest (HU); Istvan Hegedus, Budapest (HU); Eva Werkne Papp, Budapest (HU); Judit Nagyne Bagdy, Budapest (HU); Agnes Piller, Budapest (HU)

(73) Assignee: Richter Gedeon Vegyeszeti Gyar Rt., Budapest (HU)

( * ) Notice: Subject to any disclaimer, the term of this patent is extended or adjusted under 35 U.S.C. 154(b) by 255 days.

(21) Appl. No.: 10/667,201

(22) Filed: Sep. 22, 2003

(65) Prior Publication Data

US 2004/0106804 A1 Jun. 3, 2004

Related U.S. Application Data

(63) Continuation-in-part of application No. PCT/HU01/00033, filed on Mar. 23, 2001.

(51) Int. Cl.
*C07D 403/06* (2006.01)
(52) U.S. Cl. ........................................ 548/266.6
(58) Field of Classification Search .............. 548/266.6
See application file for complete search history.

(56) References Cited

U.S. PATENT DOCUMENTS

| | | | |
|---|---|---|---|
| 4,404,216 A | | 9/1983 | Richardson |
| 5,371,101 A | * | 12/1994 | Itoh et al. ........ 514/383 |
| 5,707,976 A | | 1/1998 | Kreidl et al. |
| 5,872,258 A | * | 2/1999 | Clive et al. ........ 548/266.6 |

FOREIGN PATENT DOCUMENTS

| | | |
|---|---|---|
| ES | 549020 | 3/1986 |
| ES | 549022 | 3/1986 |
| ES | 2 026 416 | 4/1992 |
| GB | 2 078 719 | 1/1982 |
| GB | 2 099 818 | 12/1982 |
| GB | 2 270 521 | 3/1994 |
| WO | WO 96/20181 | 7/1996 |
| WO | WO 98/32744 | 7/1998 |

OTHER PUBLICATIONS

Gu et al., Journal of Pharmaceutical Sciences, vol. 84, No. 12, Dec. 1995, pp. 1438-1441.*

* cited by examiner

*Primary Examiner*—Laura L. Stockton
(74) *Attorney, Agent, or Firm*—Jonathan Myers; Andrew Wilford

(57) ABSTRACT

A new process is disclosed for the synthesis of fluconazole monohydrate and for crystal modifications of fluconazole which comprises the step of
hydrolyzing a silyl ether of the formula (II)

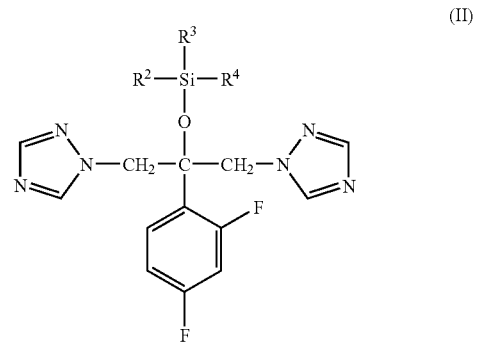

wherein
$R^2$ is hydrogen, or a $C_1$ to $C_{10}$ alkyl or phenyl group, $R^3$ and $R^4$ independently of each other are a $C_1$ to $C_{10}$ alkyl or phenyl group in an aqueous solution, preferably at a pH below 3 or above 8.

10 Claims, 6 Drawing Sheets

PROCESS FOR PREPARING MONOHYDRATE AND CRYSTAL MODIFICATIONS OF FLUCONAZOLE

CROSS REFERENCE TO RELATED APPLICATION

This application is a continuation-in-part of International Application PCT/HU01/00033, with an international filing date of 23 Mar. 2001, published in English under PCT Article 21(2) and now abandoned.

FIELD OF THE INVENTION

The invention relates to a process for the synthesis of fluconazole of formula (I) and its crystal modifications.

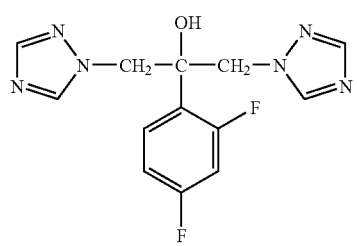

(I)

Here and further on terms crystal modification and polymorph modification have the same meaning and are used as synonyms.

BACKGROUND OF THE INVENTION

The British patent Number of 2 078 719 A describes very effective fungicide compounds, which have substantial plant growth regulating effect as well. The above compounds are illustrated by formula (A)

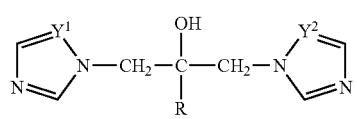

(A)

wherein the meaning of R is alkyl, cycloalkyl, aryl or aralkyl group, or the derivatives of these containing one or two halogen atoms or alkoxy, phenyl, phenoxy or trifluoromethyl substituted aryl and benzyl groups and $Y^1$ and $Y^2$ independently are —N= or —CH= group.

According to the British Patent Number of 2 099 818 A the compound 2-(2,4-difluorophenyl)-1,3-bis(1,2,4-triazole-1-yl)-propane-2-ol belonging to the above group (further on fluconazole) can be used as human fungicide too. Fluconazole is among others the active ingredient of Diflucan, which is a very effective human fungicide drug on the market.

According to the British Patent Number of 2 078 719 A propane-2-ol derivatives of formula (A) are synthesized by reacting a Grignard compound of formula R—Mg-Halogen—wherein the meaning of R is as defined above—with dichloroacetone. The so formed 1,3-dichloropropane-2-ol derivative of formula (VI)

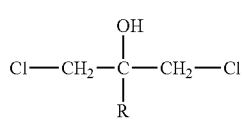

(VI)

is reacted with excess imidazole or triazole salt, for example sodium salt in protic or aprotic media (for example in dimethylformamide). The reaction can be carried out with epoxy derivatives as well, which are in situ formed from the dihalogen compound in the presence of a base by elimination of hydrogen chloride. The desired compounds can also be synthesized by reacting the appropriate 1,3-bisimidazolyl, or 1,3-bis(1,2,4-triazole-1-yl)-acetone with a Grignard compound of formula R—Mg-Halogen. According to an other synthetic pathway compounds of formula (VII)—wherein the meaning of R and $Y^1$ is as defined above

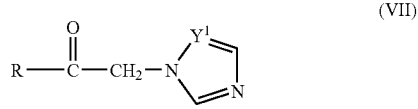

(VII)

are converted into compounds of formula (IV), containing an R substituent instead of $R^1$, with dimethyl oxosulfonium methylide,

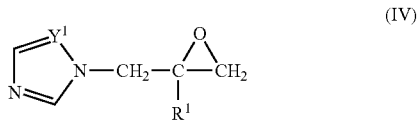

(IV)

and these are reacted with imidazole or triazole sodium salt similarly to the above-mentioned process. The starting materials are prepared according to known procedures.

The process for the synthesis of the active substance of fluconazole described in the British Patent Number of 2 099 818 A uses the compounds of formula (VI) and (IV), which contain R substituent instead of $R^1$, as starting materials, but a base and triazole are used as reagents instead of sodium triazolate.

The common feature of procedures of both patents is that the isolation of reaction products is carried out by extraction after dilution of the reaction mixture with water, followed by purification with column chromatography or vacuum distillation or other methods. The yield of the obtained product is 30–50%.

According to the Spanish Patent Number ES 549 020 A1 1 mole of 1,3-dichloroacetone is reacted with 2 mole of 1,2,4-triazole, then the 1,3-bis(1,2,4-triazole-1-yl)-propan-2-on obtained with low yield is reacted with 2,4-difluorophenylmagnesium bromide to give fluconazole. The yield is about 45% calculated on the Grignard reagent.

The common feature of the procedures described in the Spanish Patents Number of ES 549 021 A1, ES 549 022 A1 and ES 549 684 A1 is, that one or both triazolyl groups of fluconazole are introduced into the molecule with (1,2,4-triazole-1-yl)-methylmagnesium halogenide. According to the descriptions the yields are about 45–55%. The Grignard reagents containing triazolyl groups are known to be unstable, or sometimes inactive, therefor they react with low yield. During the reproduction of the procedures described in these patents the yield was always below 10%.

The Spanish Patent Number of ES 2 026 416 describes a better procedure, than the above mentioned ones. According to this 1-(1,2,4-triazole-1-yl)-2-(2,4-difluorophenyl)-3-halogen-propan-2-ol is reacted with 4-amino-1,2,4-triazole, and the obtained 1-(1,2,4-triazole-1-yl)-2-(2,4-difluorophenyl)-3-(4-amino-1,2,4-triazole-1-yl)-propan-2-ol is diazotized and the so formed diazonium salt is hydrolyzed to remove the amino group. The given yields are 78% for the first step and 85% for the second step. This process has several disadvantages from industrial point of view. The first one is, that the 3-halogen-propan-2-ol derivative used as starting material is synthesized from an epoxy derivative of formula (IV) by refluxing in a corrosive hydrogen halogenide medium. Further disadvantage is, that 4-amino-1,2,4-triazole used as reagent can only be bought as fine chemicals. The diazotation reaction and the hydrolysis of the diazonium salt on industrial scale are very dangerous procedures. Finally the combined yield of the multistep process is only 42–43%.

In the December issue of 1995 of the Journal of Ph. Sciences (Vol. 84, No. 12.) the crystal forms I and II of fluconazole, as well as the X-ray powder diffraction and Raman spectra of different crystal modifications are described without the process of their synthesis.

The Patent Number of GB 2270521 describes the synthesis of fluconazole monohydrate from anhydrous fluconazole. According to the X-ray powder diffraction data the anhydrous fluconazole, used as starting material, is identical with the crystal modification II. In this description the Patent Number of U.S. Pat. No. 4,404,219 is referred to for the synthesis of this crystal modification, but in that there is no reference for the crystal modification of the product.

OBJECT OF THE INVENTION

The object of the invention is to synthesize economically the pure or easily purifiable fluconazole final product without using reagents difficult to manage on industrial scale, and to isolate the formed fluconazole in its desired crystal modification I or II and to make possible the conversion of these different crystal modifications into each other.

SUMMARY OF THE INVENTION

The basis of our invention is the discovery that the silyl ethers of formula (II), which are the desired compounds of the U.S. Pat. No. 5,707,976,

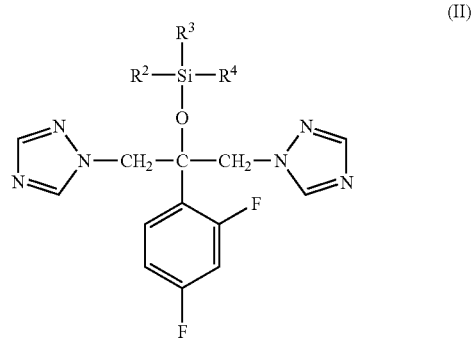

(II)

wherein the meaning of $R^2$ is hydrogen, or a $C_1$–$C_{10}$ alkyl or phenyl group, $R^3$ and $R^4$ independently of each other are a $C_1$–$C_{10}$ alkyl or phenyl groups—under aqueous acidic or basic conditions can be hydrolyzed quantitatively into fluconazole of formula (I). The compounds of formula (II) can be obtained according to the U.S. Pat. No. 5,707,976 for example from suitably substituted epoxy derivatives of formula (IV) with suitably substituted silyl triazole of formula (V)—wherein the meaning of $R^2$, $R^3$ and $R^4$ is as described above—in the presence of strong base as catalyst.

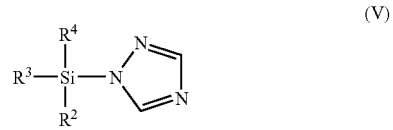

(V)

As the obtained silyl-fluconazole derivatives are very apolar, because of the presence of the trialkylsilyl group, they are easily separable from the impurities and can be synthesized economically in very pure form.

According to our invention the fluconazole monohydrate of formula (I) is synthesized by hydrolyzing a silyl ether derivative of formula (II) in an aqueous solution of pH preferably either below 3 or above 8.

The hydrolysis is a fast process. For example the trimethyl silyl ether of fluconazole is completely hydrolyzed at pH above 10 in a 10% aqueous dimethylformamide solution at room temperature in 10 min. The hydrolysis is complete under similar conditions but below pH=2 in 0.5–1 h.

The hydrolysis can be carried out under neutral conditions in homogenous phase in the presence of water, at elevated temperature, preferably at reflux temperature. The fast and industrially effective hydrolysis is preferably carried out either at pH<3 or at pH>8. The hydrolysis is very mild, unwanted byproducts are not formed even in traces, therefore very pure fluconazole can be synthesized with the hydrolysis of the properly purified silyl ether derivatives of formula (II), and can be isolated as monohydrate from the reaction mixture.

The hydrolysis is preferably carried out in homogenous phase, in a mixture of protic or aprotic dipolar solvent miscible with water and water at a pH as given above. The fluconazole formed in the reaction is preferably isolated by diluting the reaction mixture with water and cooling. As a consequence of cooling the formed fluconazole is crystallized from the reaction mixture as very pure monohydrate and can be isolated for example by filtration.

The monohydrate is stable at room temperature, it is transformed into anhydrous fluconazole, the so-called "anhydrate" between 40–90° C. with a speed depending on the conditions of the dehydration.

The polymorph modifications have different crystal structure, crystallographic constants (crystal lattice distances and energies) and therefor have different speeds of dissolution. Different polymorph modifications can be differentiated from each other by their Raman spectra. FIG. 1 and FIG. 2 show the Raman spectra between 3500.0–200.0 $cm^{-1}$ of the crystal modification I and II of fluconazole, while FIG. 3 and FIG. 4 show a section between 3300.0–2800.0 $cm^{-1}$, in which the characteristic differences for the crystal modifications I and II of fluconazole can be found.

In therapy the precondition of a reproducible permanent effect of solid pharmaceutical dosage forms (for example oral dosage forms) is that the dissolution of the active ingredient should be constant in the case of different batches. For this reason it is advisable to use always the same crystal modification of those active ingredients, which have several crystal modifications, for example fluconazole.

During the formulation the conditions of formation of crystal modification I and II were studied in detail to fulfill the morphological demands of fluconazole.

Surprisingly it was found that if the solution of anhydrous fluconazole or fluconazole monohydrate, obtained by dissolving them in a $C_1$–$C_4$ straight or branched chain alcohol at boiling temperature, is cooled slowly, preferably with a speed of 5–15° C./h, then the precipitated and dried crystals are identical with the crystal modification II of fluconazole. If the solution is cooled fast, preferably with a speed of 35–65° C./h, then the precipitated and dried crystals are identical with crystal modification I.

The crystal modification I and II can be prepared by drying the fluconazole monohydrate at different temperatures. In this case the use of appropriate seeding crystals promote the formation of the desired modification.

If the fluconazole monohydrate is dried, after seeding with crystals of crystal modification II, slowly, preferably in vacuum between 30–70° C., then the crystal modification II is formed. If the drying is carried out fast, at 80° C., then the crystal modification I is formed from fluconazole monohydrate.

According to the invention the process for the synthesis of monohydrate and crystal modifications of fluconazole of formula (I) is as follows a.) hydrolyzing a silyl ether derivative of formula (II)

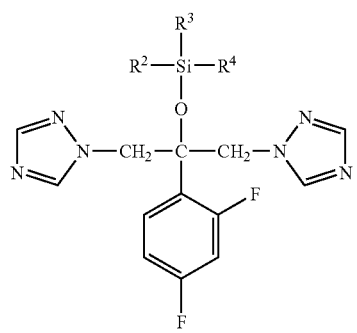

(II)

wherein the meaning of $R^2$ is hydrogen, or a $C_1$–$C_{10}$ alkyl or phenyl group, $R^3$ and $R^4$ independently of each other are a $C_1$–$C_{10}$ alkyl or phenyl group—at a pH preferably either below 3 or above 8 in an aqueous solution, then cooling the obtained reaction mixture containing the fluconazole of formula (I) and isolating the precipitated fluconazole monohydrate and optionally the fluconazole monohydrate is dissolved in a $C_1$–$C_4$ straight or branched chain alcohol at boiling temperature and the solution is cooled with a speed of 5–15° C./h to obtain the crystal modification of II of fluconazole, or b.) fluconazole monohydrate is dissolved in a $C_1$–$C_4$ straight or branched chain alcohol at boiling temperature and the solution is cooled with a speed of 5–15° C./h to obtain the crystal modification of II of fluconazole, or c.) fluconazole monohydrate is dried slowly after seeding preferably with seeding crystal of crystals modification II at 30–70° C., preferably in vacuum to obtain the crystal modification II of fluconazole, or d.) fluconazole monohydrate is dried fast after seeding preferably with seeding crystal of crystal modification I at 80° C., to obtain the crystal modification I of fluconazole.

The alcohols used in the crystallization can be branched chain alcohols, preferably isopropanol or sec-butanol or straight chain alcohols, preferably ethanol. The water content of the $C_1$–$C_4$ straight or branched chain alcohols used in the crystallization can even reach 5%. Therefor purum quality is sufficient in the case of 96% ethanol. The best results are obtained with the use of isopropanol.

Table I shows the X-ray powder diffraction (XRPD) data of crystal modifications I and II of fluconazole as measured on samples of Examples 2 and 5. (Philips PW 1840 X-ray powder diffraction meter; CuKα radiation by 30 kV and 30 mA; velocity of the goniometer: 0.05°2θ/s; sensitivity: 2×10³ cps; T.C.: 5 s; gap width: 0.05 mm).

TABLE I

| Crystal modification I, Example 2 | | | Crystal modification II, Example 5 | | |
|---|---|---|---|---|---|
| Angle [°2θ] | d [nm] | Rel. int. [%] | Angle [°2θ] | d [nm] | Rel. int. [%] |
| 10.000 | 0.8838 | 15.8 | 11.775 | 0.7509 | 8.7 |
| 13.615 | 0.6498 | 6.3 | 14.880 | 0.5949 | 12.7 |
| 14.957 | 0.5918 | 3.0 | 15.905 | 0.5568 | 18.7 |
| 16.150 | 0.5484 | 59.6 | 17.470 | 0.5072 | 50.3 |
| 16.535 | 0.5357 | 76.1 | 18.630 | 0.4759 | 14.0 |
| 17.461 | 0.5075 | 3.0 | 19.813 | 0.4477 | 28.2 |
| 18.751 | 0.4729 | 5.0 | 20.117 | 0.4410 | 28.2 |
| 20.035 | 0.4428 | 100.0 | 22.345 | 0.3975 | 4.0 |
| 21.020 | 0.4223 | 25.2 | 24.575 | 0.3619 | 100.0 |
| 21.980 | 0.4041 | 10.8 | 25.105 | 0.3544 | 42.4 |
| 23.610 | 0.3765 | 6.3 | 26.970 | 0.3303 | 36.9 |
| 24.945 | 0.3567 | 14.4 | 29.380 | 0.3038 | 38.2 |
| 25.605 | 0.3476 | 40.9 | 31.470 | 0.2840 | 33.4 |
| 27.390 | 0.3254 | 16.1 | 34.715 | 0.2582 | 6.5 |
| 28.160 | 0.3166 | 4.0 | 36.975 | 0.2429 | 6.9 |
| 29.230 | 0.3053 | 37.4 | | | |
| 29.905 | 0.2985 | 3.0 | | | |
| 30.739 | 0.2906 | 3.0 | | | |
| 32.455 | 0.2756 | 7.0 | | | |
| 34.405 | 0.2605 | 3.3 | | | |
| 35.980 | 0.2494 | 10.5 | | | |

FIG. 5 and FIG. 6 show the X-ray powder diffraction patterns (XRPD) of the samples of Examples 2 and 5. The X-ray powder diffraction patterns of samples of Examples 3, 8 and 9 and Examples 6 and 7 are the same as of Examples 2 and 5, respectively.

BRIEF DESCRIPTION OF THE DRAWINGS

FIG. 3 is a Raman spectrogran of crystal modification I of fluconazole taken over a range of 3300.0 to 2800.0 cm$^{-1}$.

Figure 1:
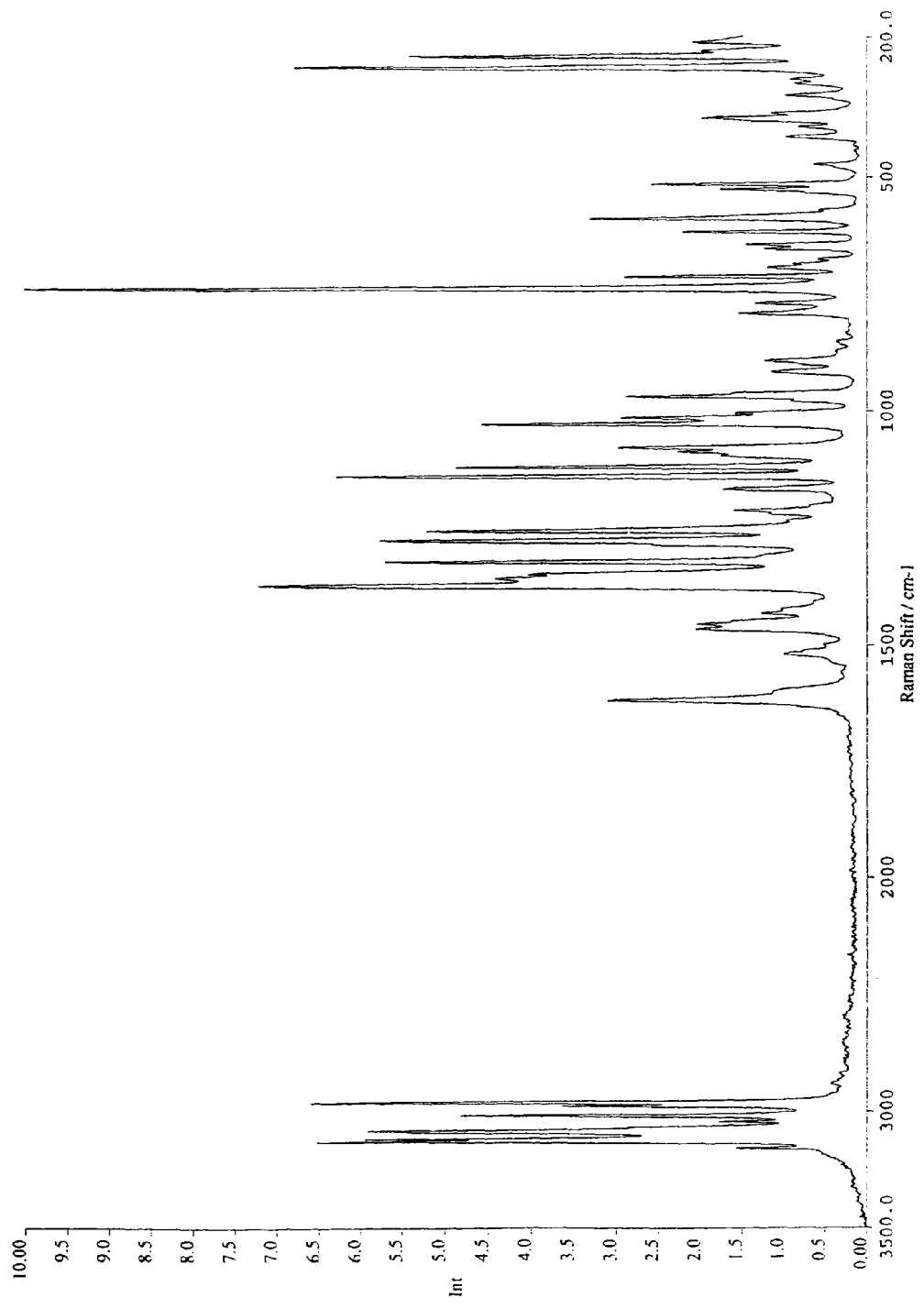
FIG. 1 is a Raman spectrogran of crystal modification I of fluconazole taken over a range of 3500.0 to 200.0 cm$^{-1}$.
Figure 2:
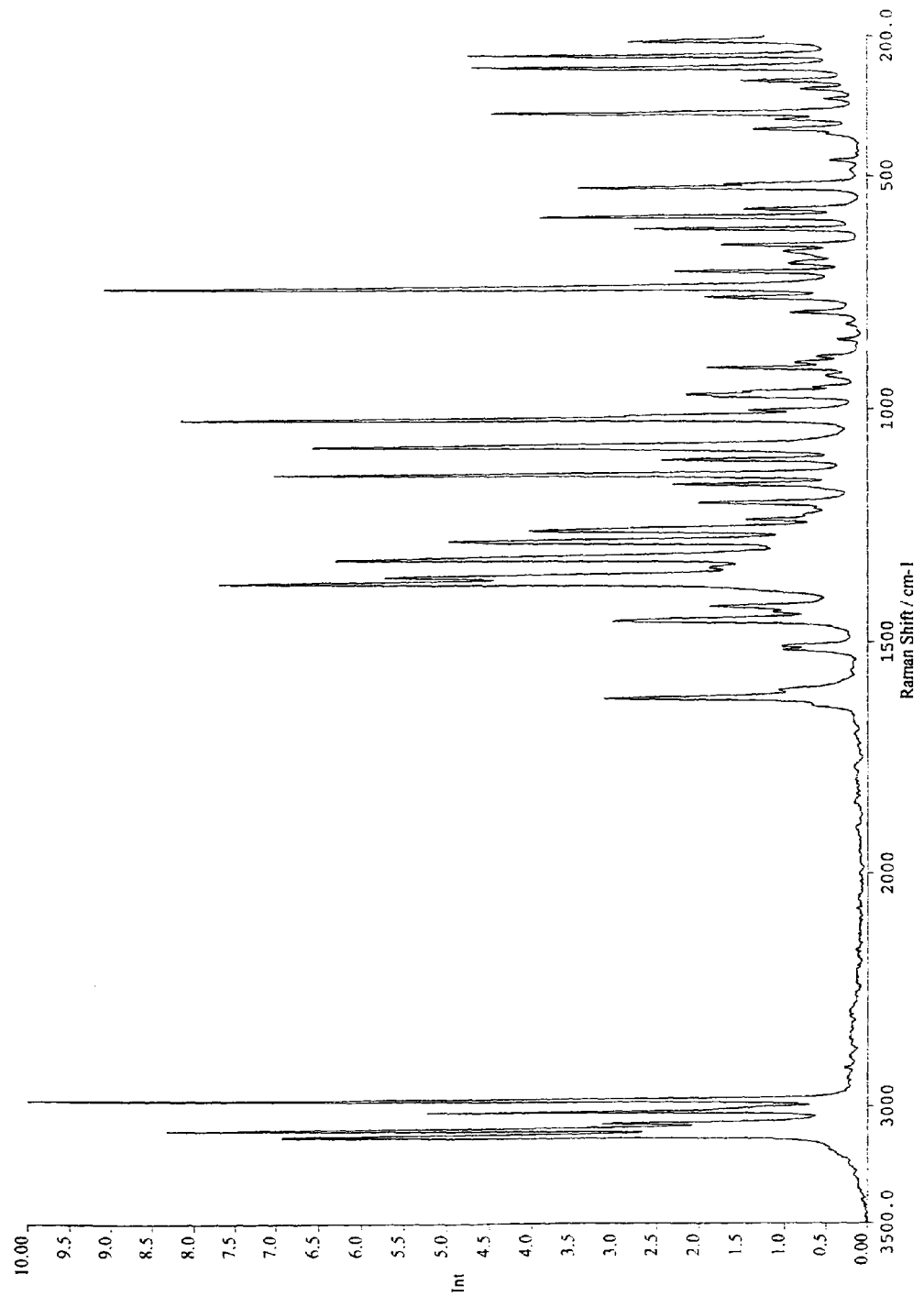
FIG. 2 is a Raman spectrogran of crystal modification II of fluconazole taken over a range of 3500.0 to 200.0 cm$^{-1}$.
Figure 7:
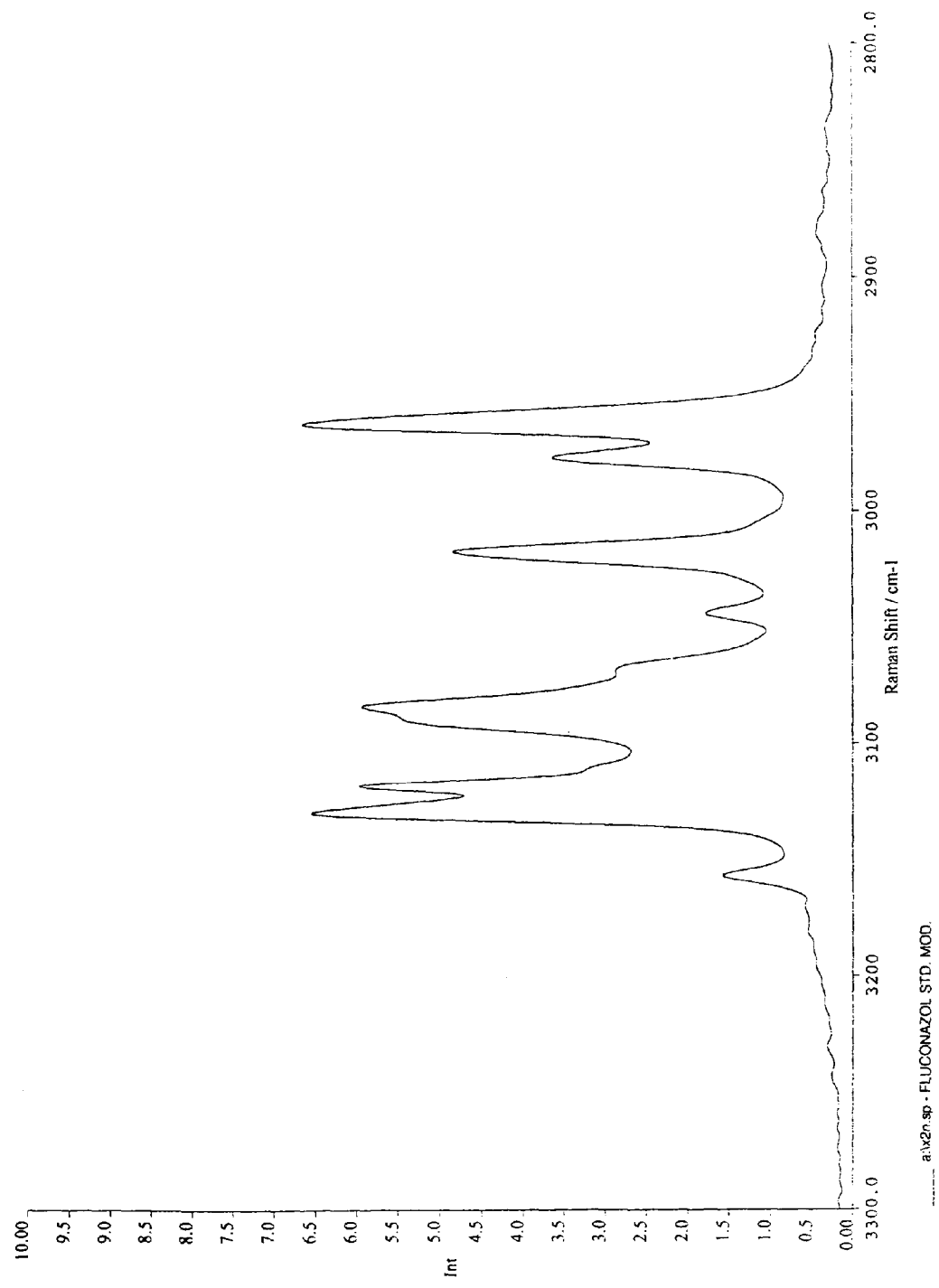
Figure 4:
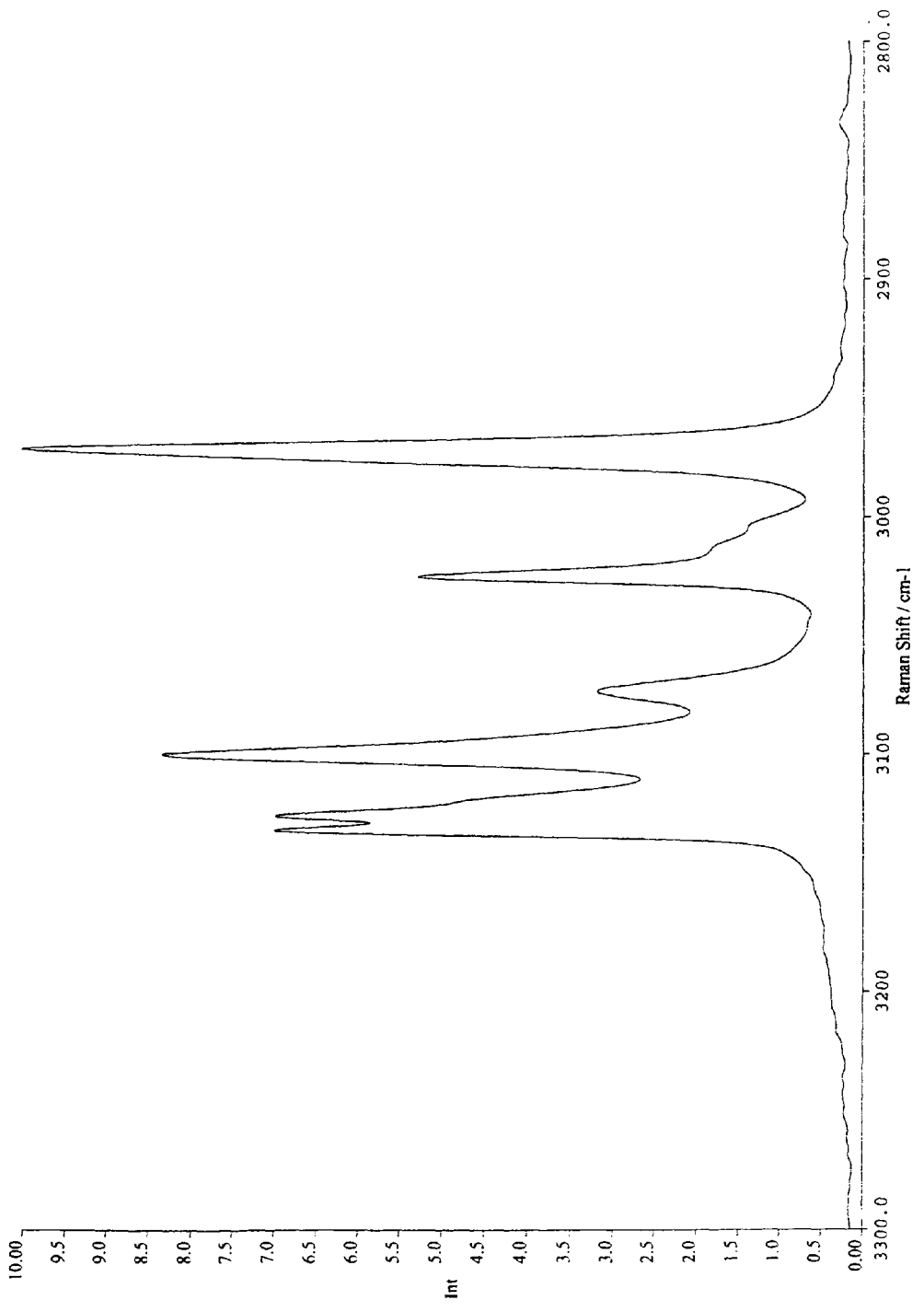
FIG. 4 is a Roman spectrogran of crystal modification II of fluconazole taken over a range of 3300 to 2800 cm$^{-1}$.
Figure 5:
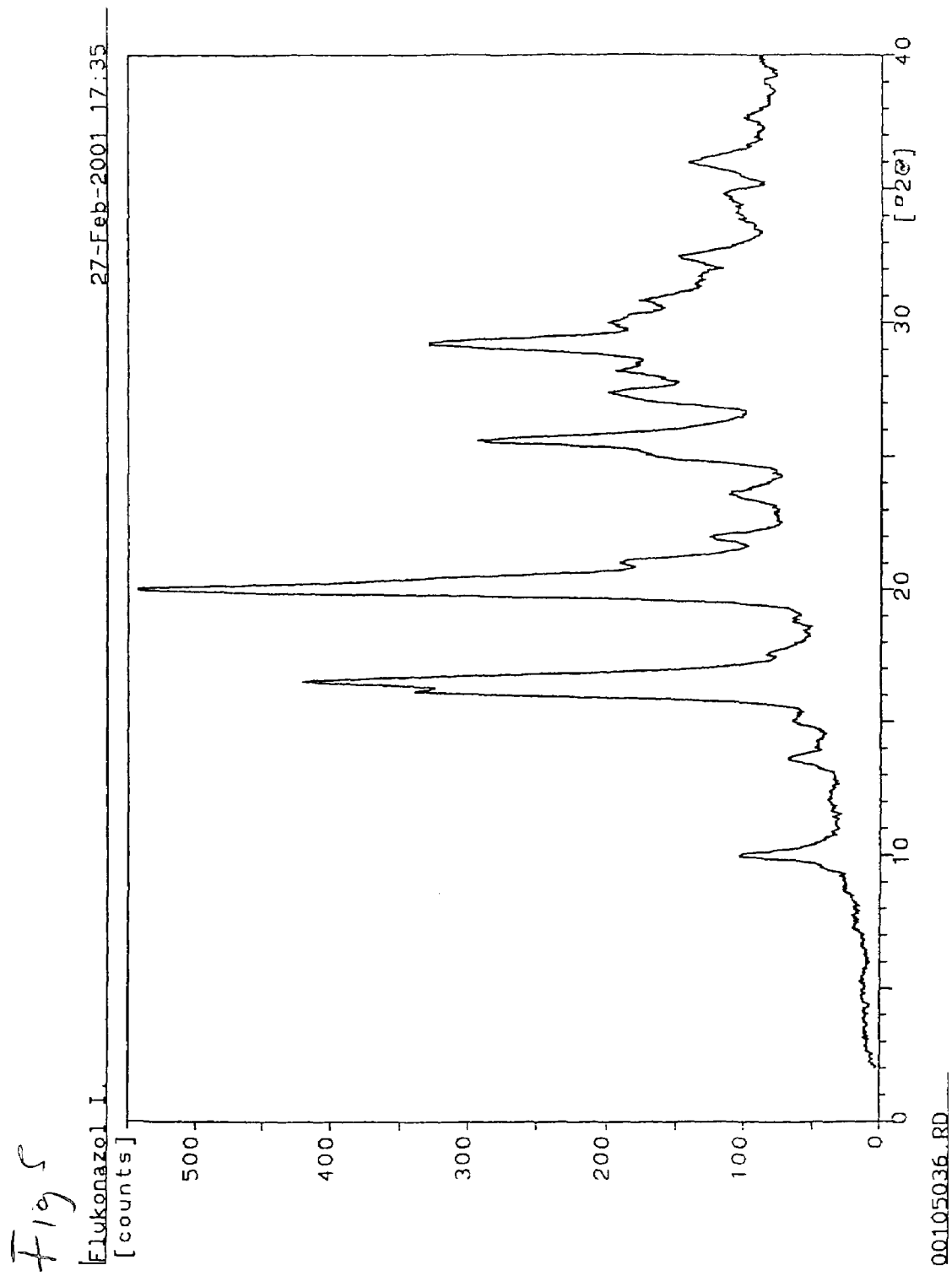
FIG. 5 is an x-ray powder diffraction pattern of a sample of crystal modification I of fluconazole.
Figure 6:
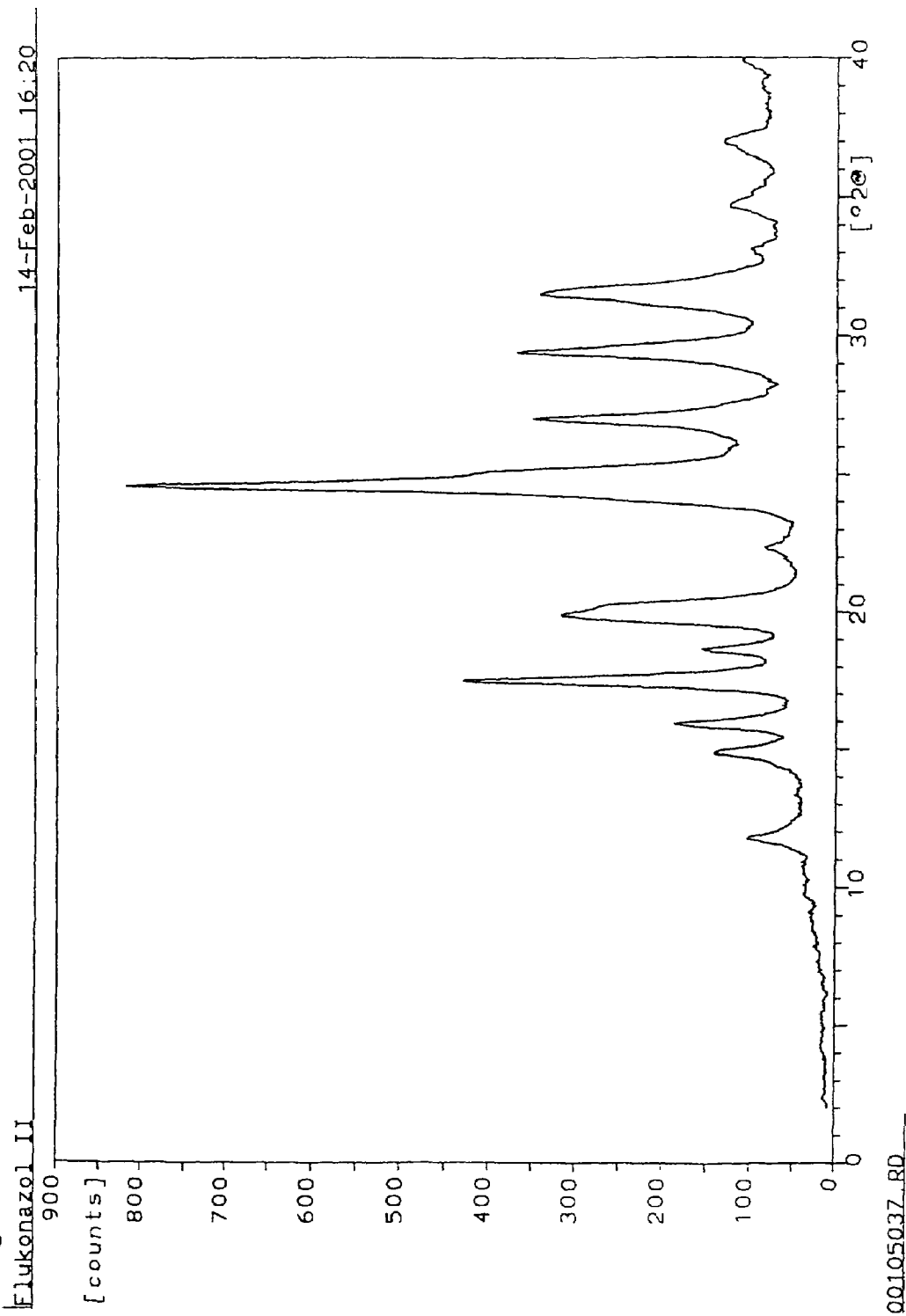
FIG. 6 is an x-ray powder diffraction pattern of a sample of crystal modification II of fluconazole.

The process according to the invention is illustrated by the following not limiting Examples.

EXAMPLE 1

2-(2,4-Difluorophenyl)-1,3-bis(1,2,4-triazole-1-yl)-propane-2-ol monohydrate

A mixture of 7.50 g (0.02 mol) of 2-(2,4-difluorophenyl)-1,3-bis(1,2,4-triazole-1-yl)-2-(trimethylsilyloxy)propane, 25 ml of methanol, 2 ml of water and 1.0 ml of concd. hydrochloric acid was stirred at 30° C. for 1 h. The reaction mixture was concentrated to a volume of 10 ml and after adding 50 ml of water the pH of the hot solution was adjusted to 8 with 10% aqueous sodium hydroxide. After cooling the precipitated crystals were filtered off, and dried at 40° C. until the weight was constant to yield 6.06 g (93.5%) of the title compound. M.p.: 139–140° C.

EXAMPLE 2

Synthesis of Crystal Modification I of Fluconazole

A mixture of 7.5 g (0.02 mol) of 2-(2,4-difluorophenyl)-1,3-bis(1,2,4-triazole-1-yl)-2-(trimethylsilyloxy)propane, 40 ml of methanol, 3 ml of water and 0.1 g of sodium hydroxide was stirred at room temperature for 1 h. After adding 300 ml of water the solution was concentrated to a volume of 50 ml with vacuum distillation. The obtained suspension was cooled to 0° C. and filtered. The obtained product was 6.12 g, water content was 11.5%. After drying at 80° C. 5.35 g of title compound was obtained. Yield: 87.4%. Mp.: 139–141° C.

EXAMPLE 3

Synthesis of Crystal Modification I of Fluconazole

A mixture of 7.5 g (0.02 mol) of 2-(2,4-difluorophenyl)-1,3-bis(1,2,4-triazole-1-yl)-2-(trimethylsilyloxy)propane, 40 ml of methanol, 3 ml of water and 0.1 g of sodium hydroxide was stirred at room temperature for 1 h. After adding 300 ml of water the solution was concentrated to a volume of 50 ml with vacuum distillation. The obtained suspension was cooled to 0° C. and filtered. The obtained product was 6.12 g, water content was 11.5%. This was placed into a 100 ml flask and 0.1 g of crystal modification I of fluconazole seeding crystals were added thereto. The compound was dried on rotary evaporator at 80° C. for 3–4 h, until the weight was constant. 5.45 g of title compound was obtained. Yield: 87.4%. Mp.: 139–141° C.

EXAMPLE 4

Synthesis of Fluconazole Monohydrate

A mixture of 7.58 g (0.02 mol) of 2-(2,4-difluorophenyl)-1,3-bis(1,2,4-triazole-1-yl)-2-(trimethylsilyloxy)propane, 0.04 g of sodium hydroxide and 70 ml of water was stirred at 80° C. for 10 min. Then 0.5 g of charcoal was added and the hot solution was filtered. The filtrate was cooled to 0° C. The precipitated crystals were filtered off and dried at 40° C. until the weight was constant to yield 5.98 g (92.1%) of the title compound. Water content 5.6%, Mp.: 139–140° C.

EXAMPLE 5

Synthesis of Crystal Modification II of Fluconazole 6.12 g (0.02 mol) of anhydrous fluconazole was dissolved in 60 ml of isopropanol with stirring at 70° C., and then the solution was cooled. After the temperature reached 50° C. the speed of cooling was 10° C./h. The precipitation of crystals started at about 40° C. After 5 h, when the temperature reached 0° C. the crystal modification II of fluconazole was filtered, and dried at 50° C. until the weight was constant to yield 5.58 g (91.2%) of the title compound. Mp.: 139–141° C.

EXAMPLE 6

Synthesis of Crystal Modification II of Fluconazole 6.12 g (0.02 mol) of fluconazole was dissolved in 25 ml of ethanol with stirring at 50° C., then the solution was cooled slowly, with constant speed (10° C./h) to 0° C. The precipitation of crystals started at about 40° C. The precipitated crystal modification II of fluconazole was filtered off and dried at 50° C. until the weight was constant to yield 5.23 g (85.5%) of the title compound. Mp.: 139–140° C.

EXAMPLE 7

Synthesis of Crystal Modification II of Fluconazole 6.12 g (0.02 mol) of fluconazole was dissolved in 60 ml of sec-butanol at 60° C., then the solution was cooled to 0° C. with a speed of 10° C./h. The precipitation started at about 42° C. The crystals were filtered and dried at 50° C. until the weight was constant to yield 5.70 g (93.1%) of the title compound. Mp.: 139–140° C.

EXAMPLE 8

Synthesis of Crystal Modification I of Fluconazole 6.12 g (0.02 mol) of fluconazole was dissolved in 60 ml of isopropanol at 70° C. The solution was cooled to 0° C. during 1 h. The precipitated crystals were filtered off and dried at 50° C. until the weight was constant to yield 5.59 g (91.3%) of the title compound. Mp.: 139–141° C.

EXAMPLE 9

Synthesis of Crystal Modification I of Fluconazole 6.12 g (0.02 mol) of fluconazole was dissolved in 20 ml of ethanol at 55° C., then the solution was cooled to 0° C. during 1 h. The precipitated crystals were filtered off and dried at 50° C. to yield 5.28 g (86.3%) of the title compound. Mp.: 138–140° C.

We claim:

1. A process for the synthesis of monohydrate and crystal modifications of fluconazole of formula (I)

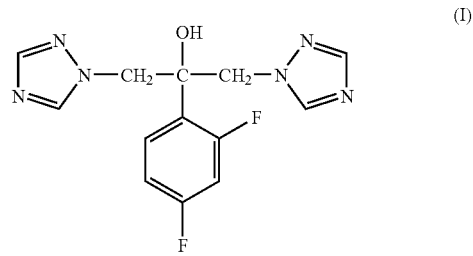

comprising the steps of:

a.) hydrolyzing a silyl ether derivative of formula (II)

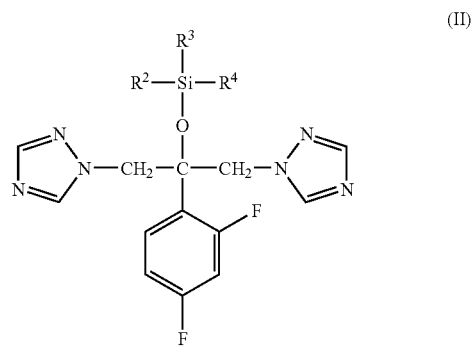

wherein the meaning of $R^2$ is hydrogen, or a $C_1$–$C_{10}$ alkyl or phenyl group, $R^3$ and $R^4$ independently of each other are a $C_1$–$C_{10}$ alkyl or phenyl group—at a pH preferably either below 3 or above 8 in an aqueous solution, then cooling the obtained reaction mixture containing the fluconazole of formula (I) and isolating the precipitated fluconazole monohydrate and optionally dissolving the fluconazole monohydrate obtained from the hydrolysis of silyl-fluconazole in a $C_1$–$C_4$ straight or branched chain alcohol at boiling temperature and cooling the solution with a speed of 5–15° C./h to obtain the crystal modification II of fluconazole, or b.) dissolving anhydrous fluconazole or monohydrate of it in a $C_1$–$C_4$ straight or branched chain alcohol at boiling temperature and cooling the solution with a speed of 5–15° C./h to obtain the crystal modification II of fluconazole, or c.) drying slowly fluconazole monohydrate after seeding preferably with seeding crystals of crystal modification II at 30–70° C., preferably in vacuum to obtain the crystal modification II of fluconazole, or d.) drying fast fluconazole monohydrate after seeding preferably with seeding crystals of crystal modification I at 80° C., to obtain the crystal modification I of fluconazole.

2. The process according to claim 1, characterized by carrying out the hydrolysis of silyl ether derivatives of formula (II)—wherein the meaning of $R^2$, $R^3$ and $R^4$ is as defined in claim 1—in aqueous methanolic solution in the presence of sodium hydroxide.

3. The process according to claim 1, characterized by carrying out the hydrolysis of silyl ether derivatives of formula (II)—wherein the meaning of $R^2$, $R^3$ and $R^4$ is as defined in claim 1—in aqueous sodium hydroxide solution.

4. The process according to claim 1, characterized by using a silyl ether derivative of formula (II), wherein $R^2$, $R^3$ and $R^4$ are methyl groups, as starting material.

5. The process according to claim 1 for the synthesis of crystal modification II of fluconazole, characterized by cooling the solution of anhydrous fluconazole or monohydrate of it in isopropanol obtained at boiling temperature with a speed of 10° C./h.

6. The process according to claim 1 for the synthesis of crystal modification II of fluconazole, characterized by cooling the solution of anhydrous fluconazole or monohydrate of it in ethanol obtained at boiling temperature with a speed of 10° C./h.

7. The process according to claim 1 for the synthesis of crystal modification II of fluconazole, characterized by cooling the solution of anhydrous fluconazole or monohydrate of it in sec-butanol obtained at boiling temperature with a speed of 10° C./h.

8. The process according to claim 5 characterized by cooling the solutions to 0° C.

9. The process according to claim 1 for the synthesis of crystal modification II of fluconazole, characterized by drying the fluconazole monohydrate in the presence of seeding crystals of crystal modification II with stirring, in vacuum at 40° C. for 2 h, then at 70° C. for 4 h.

10. The process according to claim 1 for the synthesis of crystal modification I of fluconazole, characterized by drying the fluconazole monohydrate in the presence of seeding crystals of crystal modification I with stirring, in vacuum at 80° C. for 4 h until the weight is constant.

* * * * *